(12) United States Patent
Palmer et al.

(10) Patent No.: US 9,155,289 B2
(45) Date of Patent: Oct. 13, 2015

(54) METHODS CONCERNING PPAR DELTA AND ANTAGONISTS THEREOF

(75) Inventors: Colin Palmer, Dundee (GB); John Foerster, Dundee (GB); Nainamalai Sitherswaran, Dundee (GB)

(73) Assignee: University Court of the University of Dundee, Dundee (GB)

(*) Notice: Subject to any disclaimer, the term of this patent is extended or adjusted under 35 U.S.C. 154(b) by 225 days.

(21) Appl. No.: 13/057,113

(22) PCT Filed: Jul. 31, 2009

(86) PCT No.: PCT/GB2009/050967
§ 371 (c)(1),
(2), (4) Date: Jun. 30, 2011

(87) PCT Pub. No.: WO2010/013071
PCT Pub. Date: Feb. 4, 2010

(65) Prior Publication Data
US 2011/0263691 A1 Oct. 27, 2011

(30) Foreign Application Priority Data

Aug. 1, 2008 (GB) .................................. 0814094.9
Dec. 5, 2008 (GB) .................................. 0822240.8

(51) Int. Cl.
*A01K 67/00* (2006.01)
*A01K 67/027* (2006.01)
*C07K 14/47* (2006.01)
*C12N 15/85* (2006.01)

(52) U.S. Cl.
CPC ......... *A01K 67/0275* (2013.01); *C07K 14/4702* (2013.01); *C12N 15/8509* (2013.01); *A01K 2207/15* (2013.01); *A01K 2207/20* (2013.01); *A01K 2217/00* (2013.01); *A01K 2217/052* (2013.01); *A01K 2217/203* (2013.01); *A01K 2227/105* (2013.01); *A01K 2267/0368* (2013.01); *C12N 2830/008* (2013.01); *C12N 2840/002* (2013.01)

(58) Field of Classification Search
None
See application file for complete search history.

(56) References Cited

FOREIGN PATENT DOCUMENTS

WO 97/38093 10/1997

OTHER PUBLICATIONS

Nebert et al. Biochemical Pharmacol Feb. 1997;53:249-54.*
Houdebine, J. Biotech. 1994;34, 269-87.*
Mullins, J Clin Invest, 1996;97:1557-60.*
Wall, J Dairy Sci 1997;80:2213-24.*
Kino et al. Eur J Clin Invest 2007;37:425-33.*
Michalik et al. Biochim Biophys Acta 2007;1771:991-8.*
Schön, Exp Dermatol 2008;17:703-12.*
Girroir et al. Biochem Biophys Res Comm 2008;371:456-61.*
Tan et al. Genes Dev 2001;15:3263-77.*
Int'l Search Report for PCT/GB2009/05967, four pages, mailed Jan. 21, 2010.
Written Opinion for PCT/GB2009/050967, nine pages, mailed Jan. 21, 2010.
Campbell et al. "Regulation of the *CyP1A1*promoter in transgenic mice: An exquisitely sensitive on-off system for cell specific gene regulation" *Journal of Cell Science*, vol. 109, No. 11, pp. 2619-2625 (Jan. 1996).
Kuenzli & Saurat "Effect of topical PPARβ/δ and PPARγ agonists on plaque psoriasis. A pilot study" *Dermatology*, vol. 206, No. 3, pp. 252-256 (Jan. 2003).
Romanowska et al. "PPARδ enhances keratinocyte proliferation in psoriasis and induces herapin-binding EGF-like growth factor" *Journal of Investigative Dermatology*, vol. 128. No. 1, pp. 110-124 (Jan. 2008).
Romanowska et al. "Th17 dependent psoriasis-like skin disease in transgenic mice upon activation of PPAR delta" *Journal of Investigative Dermatology*, vol. 129, suppl. 1, p. S16 (May 2009).
Sano et al. "Stat3 Links activated keratinocytes and immunocytes required for development of psoriasis in a novel transgenic mouse model" *Nature Medicine*, vol. 11, No. 1, pp. 43-49 (Jan. 2005).
Schön "Animal model of psoriasis: A critical appraisal" *Experimental Dermatology*, vol. 17, No. 8, pp. 703-712 (Aug. 2008).
Shearer et al. "Identification and characterization of a selective peroxisome proliferator-activated receptor β/δ (NR1C2) antagonist" *Molecular Endocrinology*, vol. 22, No. 2, pp. 523-529 (Feb. 2008).
Wang et al. "Regulation of muscle fiber type and running endurance by PPARδ" *PLOS Biology*, vol. 2, No. 10, E294, pp. 1532-1539 (Oct. 2004).
Westergaard et al. "Expression and localization of peroxisome proliferator-activated receptors and nuclear factor κB in normal and lesional psoratic skin" *Journal of Investigative Dermatology*, vol. 121, No. 5, pp. 1104-1117 (Nov. 2003).
Barish et al. "PPARδ: A dagger in the heart of the metabolic syndrome" *J. Clin. Invest.*, vol. 116, No. 3, pp. 590-597 (Mar. 2006).
Nickoloff et al. "Is psoriasis a T-cell disease?" *Exp. Dermatol.*, vol. 9, No. 5, pp. 359-375 (Oct. 2000).
Tan et al. "The nuclear horomone receptor PPAR-β/δ potentiates cell chemotactism, polarisation and migration" *Mol. Cell. Biol.*, vol. 27, No. 20, pp. 7161-7175 (Oct. 2007).
Woo et al. "ERK5 activation inhibits inflammatory responses via peroxisome proliferators-activated receptor δ (PPARδ) stimulation" *J. Biol. Chem.*, vol. 281, No. 43, pp. 32164-32174 (Oct 2006).

* cited by examiner

*Primary Examiner* — Janice Li
(74) *Attorney, Agent, or Firm* — Nixon & Vanderhye PC

(57) ABSTRACT

Non-human animals which overexpress PPARd or which express transgenic PPARd are useful as models for inflammatory skin conditions such as psoriasis. Test substances can be screened to assess their suitability for the treatment of inflammatory skin conditions such as psoriasis. Methyl 3-({[2-(methoxy)-4-phenyl]amino}sulfonyl)-2-thiophenecarboxylate can be administered topically for the prevention or treatment of psoriasis.

22 Claims, 6 Drawing Sheets

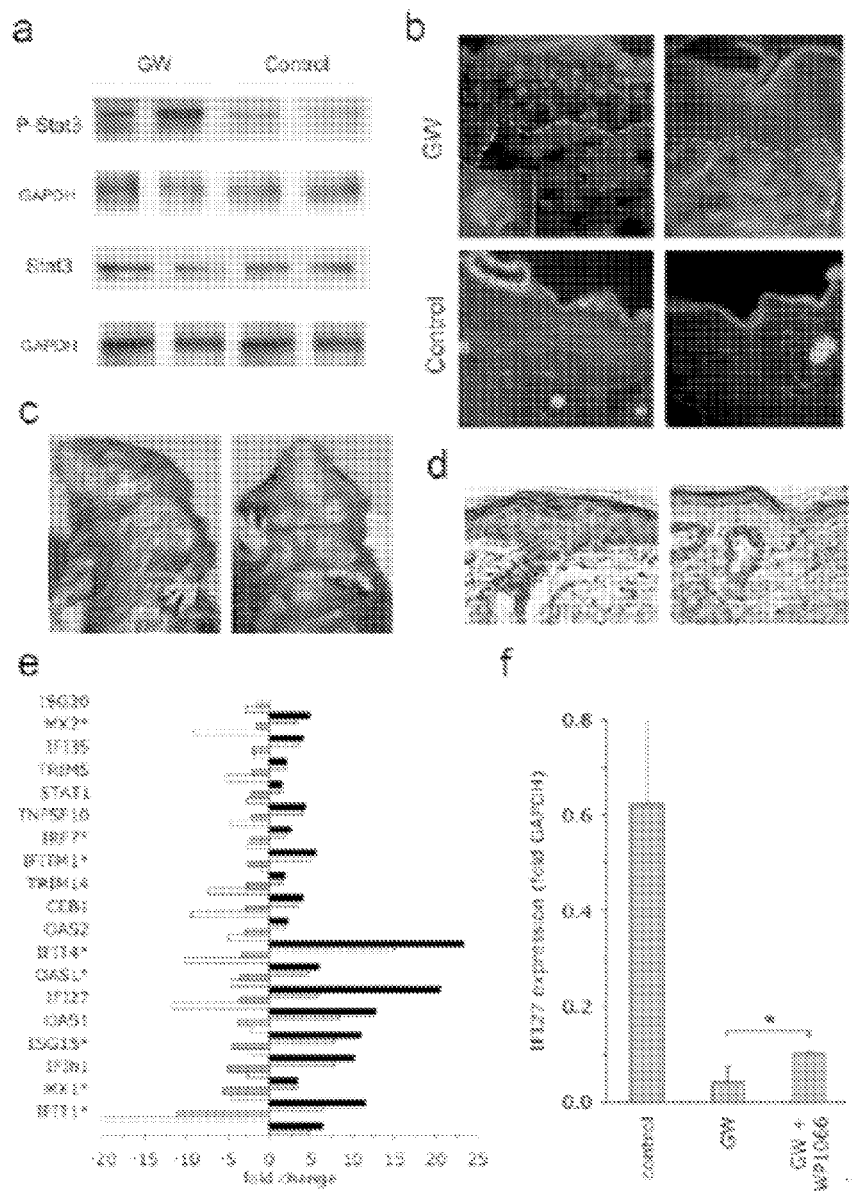
Fig. 6a-f

METHODS CONCERNING PPAR DELTA AND ANTAGONISTS THEREOF

This application is the U.S. national phase of International Application No. PCT/GB2009/050967, filed 31 Jul. 2009, which designated the U.S. and claims priority to Application No. GB 0814094.9, filed 1 Aug. 2008, and GB 0822240.8, filed 5 Dec. 2008; the entire contents of each of which are hereby incorporated by reference.

FIELD OF THE INVENTION

The present invention relates to a non-human animal which is operable to overexpress peroxisome proliferator-activated receptor delta (PPARδ) or operable to express transgenic PPARδ, in sufficient amount to display symptoms characteristic of an inflammatory skin condition, such as psoriasis, in the presence of a PPARδ agonist. The invention also relates to the use of such an animal as a model for an inflammatory skin condition, such as psoriasis, and methods of using such an animal model for identifying a substance for use in the treatment of psoriasis or another inflammatory skin condition. The invention also relates to the use of PPARδ antagonists, such as methyl 3-({[2-(methoxy)-4-phenyl]amino}sulfonyl)-2-thiophenecarboxylate, for the treatment or prevention of an inflammatory skin condition, such as psoriasis.

BACKGROUND TO THE INVENTION

Psoriasis is one of the most common skin diseases, affecting 2-4% of the Caucasian population worldwide. Due to its chronic nature, its often severely disfiguring aspect, and the lack of curative therapies, the disease causes considerable distress to individual patients and presents a significant cost burden to healthcare providers.

This complex disease is characterized by alterations in a variety of different cells.

These alterations include epidermal keratinocyte hyperproliferation and altered differentiation indicated by focal parakeratosis (cell nuclei in stratum corneum). Endothelial cells are also hyperproliferative resulting in angiogenesis and dilation, and express increased levels of adhesion molecules. A mixed leukocytic infiltrate is observed which is composed of activated T-lymphocytes, that produce inflammatory cytokines, as well as an increased number of dermal mast cells. In addition, activated dendritic cells are present which synthesize TNFα and IFNα, that are central to the disease. Intracutaneous secretion of cytokines is thought to mediate some or all of the tissue alterations which are observed in psoriasis. These cytokines include tumor necrosis factor-α (TNFα) and interleukin-1 (IL-1), vascular endothelial growth factor/vascular permeability factor (VEGF/VPF) and transforming growth factor-α (TGFα). Also of particular importance is the induction of interleukin-12 (IL12), interleukin 22, and interleukin-23 (IL23).

Research into the pathogenesis of psoriatic skin lesions, and the development of potential treatments for psoriasis, have been severely hampered by the lack of appropriate animal models. Several investigators have produced transgenic animals in which the increased expression of cytokines, adhesion molecules, signalling molecules, or other proteins in the skin results in epithelial hyperproliferation, inflammatory responses of the epidermis, or altered differentiation. For example, mouse models which overexpress VEGF-A or STAT3 in the epidermis harbour the most psoriasis-like phenotype known to date (Sano et al. (2005), "Stat3 links activated keratinocytes and immunocytes required for development of psoriasis in a novel transgenic mouse model", Nat. Med., 11, 43-39; and Xia et al. (2003) "Transgenic delivery of VEGF to mouse skin leads to an inflammatory condition resembling human psoriasis", Blood, 102, 161-168). However, none of these models is based on the modelling of up- or down-regulated molecules, as they occur in psoriatic lesional skin, and therefore may only represent "phenocopies" mimicking psoriasis. Therefore, using these models to explore novel strategies of interventions may not be relevant for the human disease and, accordingly, these models have not been widely used for pre-clinical drug testing. Moreover, none of these existing models yield a 100% disease penetrance with a rapid onset of disease, further limiting their use in high throughput screening. Finally, human psoriasis flare-ups are commonly triggered by environmental factors. One of the most important "classical" triggers of psoriasis is the so-called Koebner phenomenon which refers to the elicitation of skin pathology by mechanical trauma such as habitual friction on exposed joints, minor cuts, or surgical wounds. None of the existing animal models have been shown to exhibit a Koebner phenomenon.

Another known animal model uses human psoriatic skin transplanted onto the skin of a scid mouse. In these animal models, the transplanted skin grafts reportedly implant with greater than 85% graft survival and continue to exhibit psoriatic features for at least six weeks after transplantation. However, this animal model is difficult to utilize as a screening method for therapeutic agents as it requires human skin for transplantation to generate the model. Thus, there are no prior models of psoriasis in which the clinical and histopathological phenotype are known to develop as the result of recreating the overexpression of a gene which is known to be overexpressed in lesional psoriatic skin.

There is, therefore, an unmet need for an animal model which is suitable for investigations into psoriasis. Any such model should reproduce the clinical and histopathological phenotype of human psoriasis to as large an extent as possible. The model should be useful for research and for screening test substances which may be useful for the treatment of psoriasis. The invention aims to provide such a model and also extends to animal models which are relevant to other inflammatory skin conditions.

SUMMARY OF THE INVENTION

According to a first aspect of the present invention there is provided a method of preparing a non-human animal model for an inflammatory skin condition, the method comprising providing a non-human animal which is operable to overexpress PPARδ, or operable to express transgenic PPARδ, and administering to the non-human animal a dose of PPARδ agonist which is sufficient to mediate symptoms characteristic of the inflammatory skin condition.

Peroxisome proliferator-activated receptor delta, PPARδ (also known as PPARβ), is a nuclear receptor protein which functions as a transcription factor and contributes to the regulation of adipogenesis, glucose metabolism, myogenesis, and macrophage function. PPARδ acts as a regulator of gene transcription upon binding of activating ligands. We have found that a non-human animal which overexpresses human PPARδ, or which is operable to express transgenic PPARδ, provides an improved model of inflammatory skin conditions, such as psoriasis, when PPARδ is expressed and a PPARδ agonist is provided. Unlike the models of the prior art, the model of the present invention can mimic the clinical and histopathologic characteristics, and signalling events of human psoriasis. Rather than representing a phenocopy of an inflammatory condition, such as psoriasis, essential elements of human psoriatic signalling are re-created in vivo. Further benefits, advantages and applications of the non-human animal model are discussed below.

The inflammatory skin condition may be psoriasis. However, the non-human animal is useful as model for a wider range of inflammatory skin conditions. For example, the inflammatory skin condition may be an inflammatory skin disease involving immune disregulation and/or altered epidermal cell turnover, for example, psoriasis, a parapsoriasis disease, lichen planus, epidermal congenital nevi, pityriasis rubra pilaris, or eczema. The inflammatory skin condition may be an inflammatory skin condition involving genetic lesions located in signalling pathways related to PPAR signalling. The inflammatory skin condition may be an inflammatory skin condition involving chronic regenerative epidermal reactions, for example, wound healing, epidermal dysplasias, or papilloma-associated epidermal hyperproliferation.

The non-human animal is typically a rodent, for example, a mouse. In contrast with humans, rodents do not normally express PPARδ in their adult interfollicular skin. The non-human animal may be operable to overexpress native PPARδ, for example under the influence of an introduced promoter. However, the non-human animal may be operable to express transgenic PPARδ. Typically, the non-human animal is operable to express transgenic humanized PPARδ, such as human PPARδ. In this case, the amount of transgenic PPARδ which is expressed in use typically exceeds the amount of PPARδ which is expressed in the corresponding wild type animal, in at least some tissues, such as the sebaceous glands.

By "operable to overexpress PPARδ" or "operable to express transgenic PPARδ" we include the option that the overexpression of PPARδ, or the expression of transgenic PPARδ, is inducible, for example, because the overexpression of PPARδ, or the expression of transgenic PPARδ, are under the control of an inducible promoter. In this case, expression does not occur, or occurs only at a significantly lower level when transcription is not induced. The method may therefore include the step of inducing transcription by administering an agent which has the effect of inducing an inducible promoter. The inducible promoter may, for example, be the CYP1A promoter in which case overexpression of PPARδ, or the expression of transgenic PPARδ, may be induced by feeding Indole-3-Carbinol (I3C) to the animal. Nevertheless, with this promoter, sufficient transgenic (typically human) PPARδ to mediate at least some symptoms characteristic of psoriasis, when activated by a sufficient dose of PPARδ agonist, may be expressed even without induction, in relevant tissues including the sebaceous glands.

Typically, in order to display symptoms characteristic of the inflammatory skin condition, it is necessary to administer a PPARδ agonist, such as the ligand PPARδ activator, GW-501516k, (2-Methyl-4-((4-methyl-2-(4-trifluoromethylphenyl)-1,3-thiazol-5-yl)-methylsulfanyl)phenoxy-acetic acid). The PPARδ agonist may be administered topically.

Thus, the non-human animal may display the symptoms characteristic of psoriasis responsive to administration of both an inducer and a PPARδ agonist. Alternatively, a non-human animal may be provided which displays the symptoms characteristic of psoriasis responsive to administration of a PPARδ agonist without a requirement for an additional inducer. Preferably, the non-human animal displays no or few of the symptoms characteristic of the inflammatory skin condition in the absence of at least the PPARδ agonist or, in some embodiments, both an inducer and a PPARδ agonist.

Preferably, the non-human animal develops at least the majority, preferably at least eight, and more preferably at least nine or at least ten of the following symptoms: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, and changes in cytokine and/or gene expression patterns which correspond to changes in cytokine and/or gene expression patterns which are observed in the skin of human patients with psoriasis.

Preferably, the non-human animal displays a Koebner phenomenon, that is to say, symptoms characteristic of the inflammatory skin condition are most pronounced on body regions subjected to mechanical trauma.

The non-human animal should preferably overexpress PPARδ, or express transgenic PPARδ, in one or more types of cell, including at least keratinocytes, to thereby display symptoms characteristic of psoriasis or another inflammatory skin condition. Preferably, the non-human animal overexpresses PPARδ, or expresses transgenic PPARδ, in its sebaceous glands. Typically, the non-human animal is operable to overexpress PPARδ, or to express transgenic PPARδ, in at least some types of T-cell. It may be that the non-human animal is operable to overexpress PPARδ, or to express transgenic PPARδ, in both the skin (e.g. keratinocytes) and the spleen simultaneously. Strong symptoms characteristic of psoriasis may be obtained in such animals. It may be that the non-human animal is operable to overexpress PPARδ, or to express transgenic PPARδ, in a wide range of types of cell.

According to a second aspect of the present invention, there is provided a method of identifying a substance for use in the treatment of an inflammatory skin condition, the method comprising providing a non-human animal which is operable to overexpress PPARδ, or operable to express transgenic PPARδ, administering a dose of PPARδ agonist which would be sufficient to mediate symptoms characteristic of the inflammatory skin condition in the absence of test substance to the non-human animal, or tissues and/or cells derived therefrom, and administering a test substance to the non-human animal, or tissues and/or cells derived therefrom.

Thus, in the absence of test substance, the non-human animal, or tissues and/or cells derived therefrom, would display symptoms characteristic of the inflammatory skin condition. If, in the presence of the test substance, some or all of the symptoms which would be displayed in the absence of test substance, were reduced or absent compared to a control animal to which test substance has not been administered, this would be indicative that the test substance, or a derivative or analogue thereof, would be a candidate for use in the prevention or treatment of the inflammatory skin condition.

The inflammatory skin condition may be psoriasis.

The method may comprise the step of measuring STAT3 phosphorylation (typically Tyr-705 phosphorylation in the case of murine STAT3), or a biological indicator regulated by STAT3 phosphorlyation. We have found that STAT3 phosphorylation is regulated by PPARδ. Therefore, the potential of a test substance to be a candidate for use in the prevention or treatment of the inflammatory skin condition might be investigated by monitoring the relationship between STAT3 phosphorylation, or a biological indicator regulated by STAT3 phosphorylation, and the amount or presence of the test substance administered to the non-human animal, or tissues and/or cells derived therefrom.

Further preferred and optional features of the second aspect of the invention correspond to those discussed above in relation to the first aspect of the invention.

The invention extends in a third aspect to the use of a non-human animal which is operable to overexpresses PPARδ, or operable to express transgenic PPARδ, in sufficient amount for the non-human animal to display the symptoms of an inflammatory skin condition in the presence of a PPARδ agonist, as an animal model for an inflammatory skin condition. The inflammatory skin condition may be psoriasis.

According to a fourth aspect of the present invention, there is provided a non-human animal, in which at least some types of cell, including at least keratinocytes, are operable to overexpress PPARδ, or operable to express transgenic PPARδ, in sufficient amount for the non-human animal to display the symptoms of an inflammatory skin condition in the presence of a PPARδ agonist.

According to a fifth aspect of the present invention, there is provided a non-human animal, in which at least cells within the sebaceous glands of the non-human animal are operable to overexpress PPARδ, or operable to express transgenic PPARδ, in sufficient amount for the non-human animal to display the symptoms of an inflammatory skin condition in the presence of a PPARδ agonist.

Preferably, the overexpression of PPARδ, or the expression of transgenic PPARδ is inducible, and the non-human animal does not display the symptoms of psoriasis except when a PPARδ agonist is present and, if necessary, the overexpression of PPARδ is induced.

Preferably, the non-human animal displays symptoms of psoriasis in the presence of a PPARδ agonist.

Preferably, the non-human animal displays at least eight and more preferably at least nine or at least ten of the following symptoms in the presence of a PPARδ agonist: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, and changes in cytokine and/or gene expression patterns which correspond to changes in cytokine and/or gene expression patterns which are observed in the skin of human patients with psoriasis In the presence of a PPARδ agonist the non-human animal preferably displays increased phosphorylation of STAT3.

Preferred and optional features of the non-human animal correspond to those discussed above in relation to the non-human animals use in the first and second aspects of the invention.

The invention extends in a sixth aspect to the use of a PPARδ antagonist for the treatment or prevention of an inflammatory skin condition, for example psoriasis. The invention also extends to the use of a PPARδ antagonist for the manufacture of a medicament for the treatment of an inflammatory skin condition, for example psoriasis. The medicament may comprise a therapeutically effective amount of the PPARδ antagonist and a pharmaceutically acceptable diluent. Typically, the PPARδ antagonist is applied topically in a therapeutically effective amount. The medicament is typically suitable for topical application.

The PPARδ antagonist preferably does not significant antagonise PPARα or PPARγ.

The PPARδ antagonist is preferably methyl 3-({[2-(methoxy)-4-phenyl]amino}sulfonyl)-2-thiophenecarboxylate, or a pharmaceutically acceptable derivative thereof.

BRIEF DESCRIPTION OF THE DRAWINGS

An example embodiment of the invention will now be illustrated with reference to the following Figures:

FIG. 3(a) Cis-regulatory elements in the rat CYP1A1 promoter used to drive inducible expression of human PPARδ. Upper panel: Map of the sebaceous-specific G/C-box element and the AHR-responsive DXE/XRE cluster in the cyp1A1 promoter as well as the human human K5 promoter. Bottom panel: ClustalW alignment of promoters identified by a BLAST search using the 20 bp G/C element of the Cyp1A1 promoter. All of the genes shown were found in the top 10% percentile of all transcripts expressed in human sebaceous glands (GDS3215 at the NCBI GEO website www.ncbi.nlm.nih.gov/geo/). FIG. 3(b) illustrates immunohistochemistry using anti-PPARδ of mice transgenic for human PPARδ driven by the rat CYP1A promoter (PPARδ TG), as well as wild type mice. Magnification 200×; FIG. 3(c) illustrates immunohistochemistry of abdominal skin samples from PPARδ transgenic mice taken at the indicated times after initiation of PPARδ activation mediated by administration of the synthetic ligand GW501516 in the chow; FIG. 3(d) illustrates PPARδ immunohistochemistry 48 h after topical application of indole-3-carbinole (I3C) to the skin of PPARδ transgenic mice at 200× (left) and 400× (right) magnification;

(FIGS. 5a-5c) Gross morphology, (FIGS. 5d-5e) H&E histology of control mice not treated with GW (5d), or fourteen days after induction (5e-5g). Magnification 200× (5d,5e) or 400× (5f). (5g) Immunostaining for Ki67 of skin from PPARδ transgenic mice maintained in the absence (left) or presence (right) of GW. Magnification 200×. (5h) Induction of skin disease by topical application of either 0.3% of indole-3-carbinole (I3C, left) or I3C plus 0.3% GW501516 once daily to shaved abdominal skin. Gross macroscopic phenotype (top) and H&E histology of treated skin (bottom) was documented 10 days after beginning of treatment; and FIG. 6. Activation of STAT3 by PPARδ, (a) Western blot of whole skin samples from two GW501516-treated (GW) and two control PPAR transgenic mice, respectively, probed with anti phospho-STAT3 (top) and anti-STAT3 (bottom) along with anti-GAPDH loading controls (top-band of the STAT3 doublet represents STAT3α, bottom-band STAT3β, respectively), (b) immunofluorescence with anti phospho-STAT3 of skin from GW-treated and control PPARδ mouse in the absence (left) or presence (right) of competition with antigenic peptide. White dashed line marks dermo-epidermal boundary (not marked in control samples where epidermis is only two cell layer-thick), all samples at 400× magnification. The inset in the upper left panel (1000×) shows counter-stain with DAPI to verify nuclear localization of phospho-STAT3. (c) gross appearance of GW-fed PPARδ mouse (left) or mouse concurrently IP-injected with WP1066 (right), as detailed in Methods, (d) H&E histology of skin samples from mice shown in (d) at 200× magnification, (e) fold change of genes repressed by activated STAT3 (dark grey columns, data taken from (Dauer et al. (2005), "Stat3 regulates genes common to both wound healing and cancer." *Oncogene*, 24, 3397-3408.) in GW501516-fed vs. control PPAR (transgenic mice (white), lesional vs. non-lesional skin from psoriasis patients in the GSE14905 (black), and the GAIN (light grey) datasets, respectively. * denotes genes that did not meet a p-value<0.01 and are thus were formally excluded from cluster IV (table S2), (f) Taqman-based qPCR of IFI27 from whole skin of untreated, GW-fed, and GW-fed+WP1066-injected PPAR (mice, respectively. *p<0.05.

Experimental

Mice were generated which are inducible to overexpress human PPARδ in the skin and a wide range of other tissues and organs, including the spleen, under the control of the CYP1A1 promoter. The CYP1A1 dioxin-responsive promoter was initially chosen because it is known to be transactivated by the aryl hydrocarbon receptor (AHR) upon binding of specific AHR agonist ligands. (Campbell et al., Regulation of the CYP1A1 promoter in transgenic mice: an exquisitely sensitive on-off system for cell specific gene regulation, J. Cell Science, 1996, 109 (Pt. 11), 2619-2625).

The mice were generated by cloning full-length human PPARδ downstream of the human CYP1A1 promoter. Plasmids encoding human PPARδ were prepared by the following protocol. The coding sequences of PPARδ, were amplified using primers PRMG15 (5'-CTAG TCTAGAATGGAGCAGCCACAGGAGGAAGC-3') and PR MG3 (5'-CTAG TCTAGATTAGTACATGTCCTTGTAGATCTCCTG-3'), respectively (XbaI-sites underlined, ATG start codon in bold).

The PCR products were cleaved with XbaI and cloned in plasmid pUHD10-3 (M. Gossen, unpublished, Genbank accession number U89931) creating pMGD7 (PPARδ). The integrity of the inserts were confirmed by sequencing and cleaved out using BamHI and ligated into plasmid pAHIR1-β-gal (Campbell, 1996} cleaved with BglII, resulting in the plasmid pMGD72 (PPARδ). The proper orientations of the inserts were confirmed by restriction endonuclease analysis and sequencing. Transgenic mice were generated by microinjection of the expression unit (NotI fragment) of the plasmid pMGD72 into pro-nuclei of C57BL/J6×CBA F1 fertilized eggs. Mice were maintained under standard animal house conditions.

Figure 1:
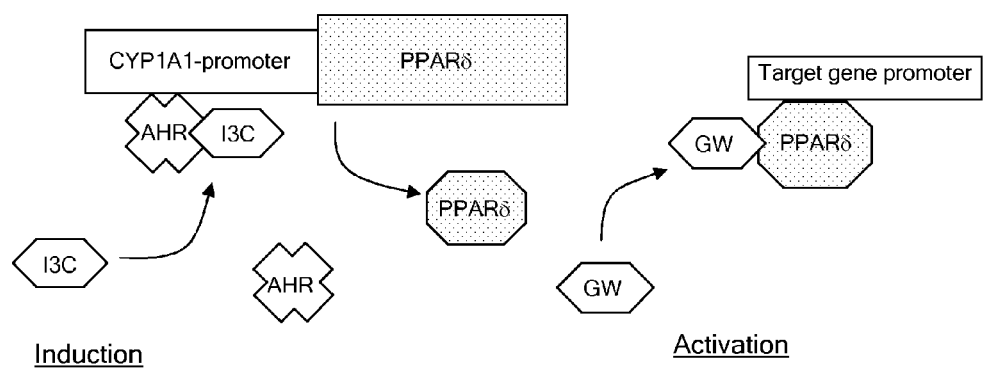
FIG. 1 is a schematic diagram of the system employed for inducible expression and activation of PPARδ in vivo.

In a first study, indole-3-carbinole (I3C) introduced into the chow at a final concentration of 0.5% (w/w), for one week, was used to induce expression of PPARδ. The resulting translated protein was conformationally activated by the specific PPARδ ligand GW-501516 (2-Methyl-4-((4-methyl-2-(4-trifluoromethylphenyl)-1,3-thiazol-5-yl)-methylsulfanyl)phenoxy-acetic acid), added in powdered form to the chow at a concentration of 0.003% (w/w) for an additional 16 days. This activation mechanism is illustrated in FIG. 1. Thus, PPARδ can be transcriptionally activated and conformationally activated by concurrent feeding with I3C and GW-501516.

Figure 2:
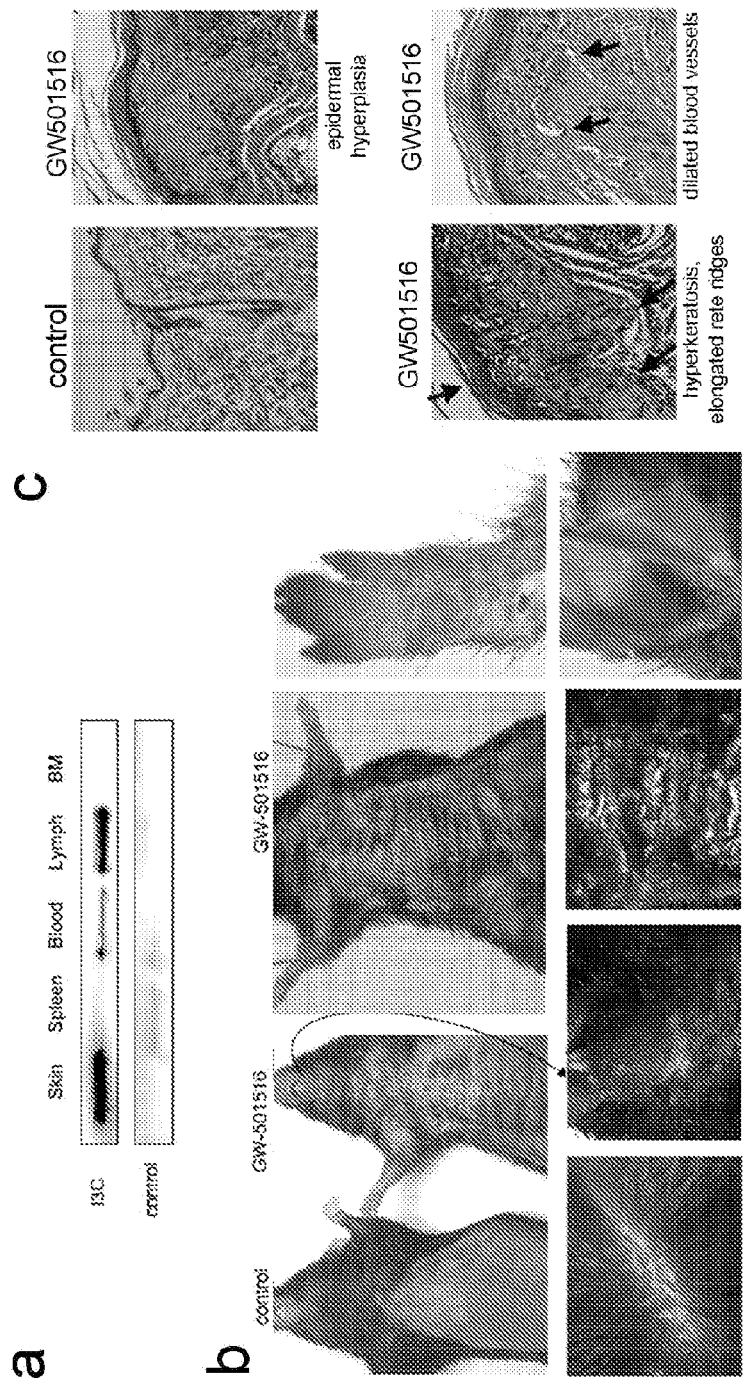
FIG. 2(a) illustrates Western blot analyses of 10 μg of total protein extract of transgenic mice fed I3C or control diet in an experiment in which PPARδ expression was induced in mice harbouring CYP1A1-controlled PPARδ by oral administration of indole-3-carbinol (I3C) for seven days (top); and an experiment in which PPARδ was expressed by feeding of I3C and activated by additional administration of the specific PPARδ ligand GW-501516 (GW) for 25 days (bottom)
FIG. 2(b) is a close-up photograph of the macroscopic phenotype of mice receiving both I3C and GW-501516 administration.
FIG. 2(c) is a photograph of standard H&E histology stains prepared from abdominal skin of the animals shown in FIG. 2(a)

The mice were prepared for the purposes of studies concerning a wide range of cancer phenotypes and liver fat accumulation. When PPARδ was induced upon feeding of I3C, strong induction of PPARδ expression was noted both in the skin and in lymph notes (FIG. 2a). When we activated the overexpressed PPARδ by additional administration of the specific PPARδ agonist ligand GW-501516, a dramatic skin phenotype was observed after 25 days, including widespread scaling, skin thickening, and inflammation (FIG. 2a, bottom and FIG. 2b). Histologically, the skin of mice harbouring activated PPARδ showed greatly expanded epidermal layers, as well as dermal infiltration of inflammatory cells (FIG. 2c). This phenotype is similar to that seen in human psoriasis. Rodents, such as mice, do not normally express PPARδ in their skin and in control experiments in which GW-501516 was administered to unmodified mice, no psoriatic symptoms were observed.

Although upregulation of PPARδ was known to be associated with psoriasis, the expression and/or activation of many proteins is known to be upregulated in psoriasis. The striking similarity of the resulting phenotype to human psoriasis indicates that the transgenic mice are suitable as animal models for investigations into psoriasis. The symptoms displayed by the transgenic mice included the following clinical and histopathological features which are also characteristic of human psoriasis: dermal and epidermal infiltration of T lymphocytes in association with erythematous skin with loose whitish scales; acanthosis, hyperkeratosis and focal parakeratosis; keratinocyte hyperproliferation; changes in epidermal differentiation markers; increased numbers of CD11c+ dendritic cells; prominent dermal angiogenesis and dilation of blood vessels; increased number of dermal mast cells, and infiltration of neutrophils. The skin phenotype is typically visible within a week and full blown within around twenty days in all mice, thus making it feasible to study its response to a variety of manipulations, or to employ the mice in high throughput screens for candidate therapeutic entities.

Figure 3:
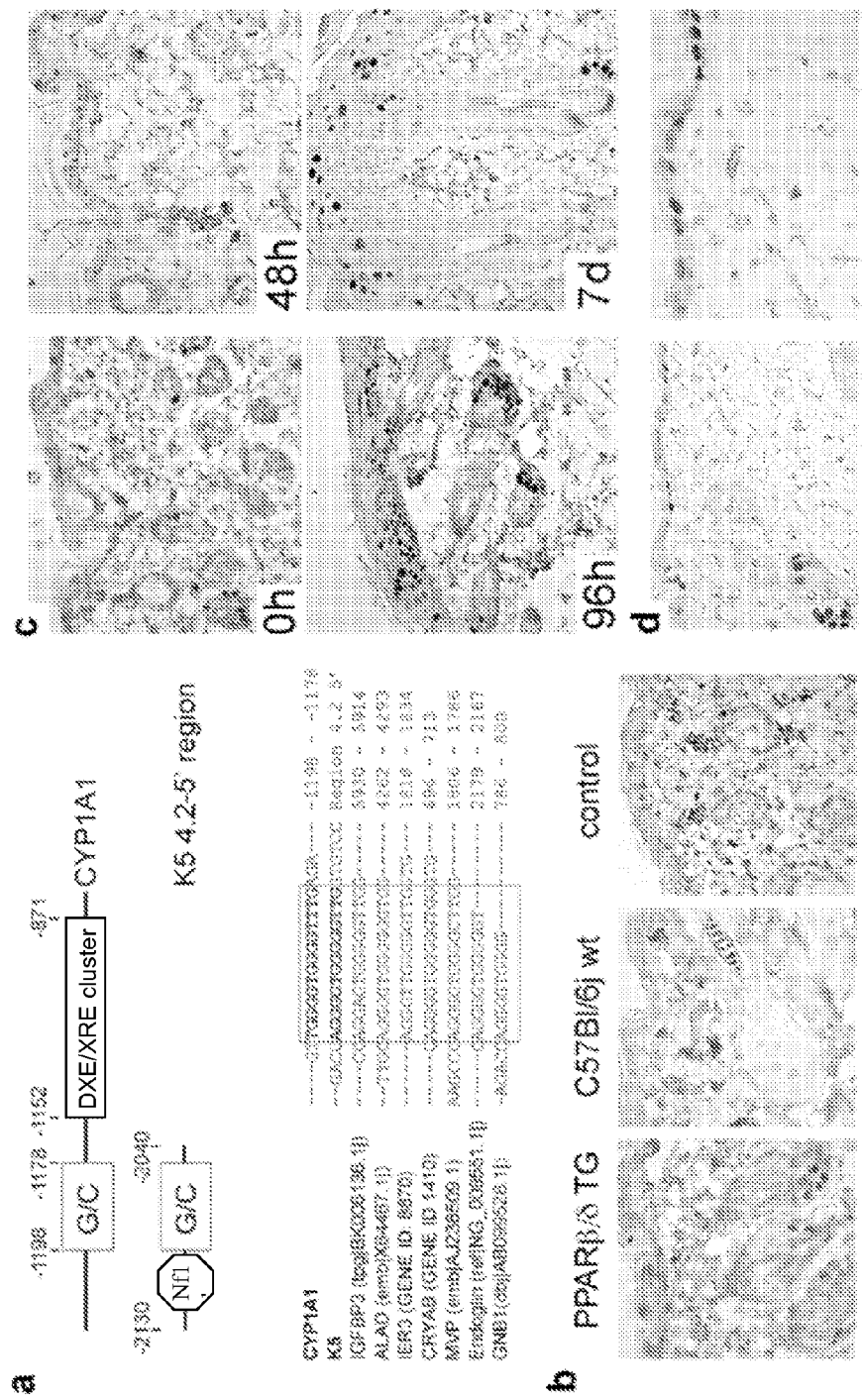
FIG. 3 illustrates experimental results from arising from the inducible expression of PPARδ in mouse epidermis.

It was discovered that induction with I3C was not required for the symptoms of psoriasis to be displayed. In addition to a well-documented DXE/XRE cluster conferring responsivity to AhR activation (Robertson et al. (1994) "Aryl hydrocarbon-induced interactions at multiple DNA elements of diverse sequence-a multicomponent mechanism for activation of cytochrome P4501A1 (CYP1A1) gene transcription", *Nucleic acids research,* 22, 1741-1749). the Cyp1A1 enhancer contains a cis-acting element conserved in the keratin 5 promoter (FIG. 3a, upper panel). This element, termed K5 4.2-5', directs AhR-independent, highly specific constitutive expression in sebaceous glands (Kaufman et al. (2002), "Dissection of a complex enhancer element: maintenance of keratinocyte specificity but loss of differentiations specificity. *Molecular and Cellular Biology.,* 22, 4293-4308.) Thus, the rat CYP1A1 promoter also drives Ahr-independent sebaceous gland-specific expression of an EGFP reporter in mice (Rowe et al. (2008), "Illuminating role of CYP1A in skin function", *The Journal of Investigative Dermatology,* 128, 110-124. We identified the K5 4.2-5' element as a universal "sebaceous box" present in the promoters of genes belonging to the top 10% of all expressed genes in sebaceous glands (FIG. 3a, bottom). Accordingly, cloning human PPARδ downstream of the same promoter efficiently conferred high constitutive sebaceous-specific expression of PPARδ (FIG. 3b). We hypothesized that activation of PPARδ in the sebaceous glands should elicit secondary expression of PPARδ in the upper epidermis via the DXE/XRE cluster in the CYP1A1 enhancer since PPARδ stimulates sebocyte differentiation (Michalik and Wahli (2007), "Peroxisome proliferator-activated receptors (PPARs) in skin health, repair and disease. *Biochimica et biophysica acta,* 1771, 991-998; Rosenfield et al. (1999), "Rat preputial sebocyte differentiation involves peroxisome proliferator-activated receptors", *J. Invest. Dermatol.,* 112, 226-232) and delivery of sebum to the skin (Trivedi et al. (2006), "Peroxisome proliferator-activated receptors increase human sebum production", *The Journal of Investigative Dermatology,* 126, 2002-2009) which, in turn, triggers epidermal delivery of lipoxygenase-products serving as endogenous AhR ligands such as LXA4 or 5,6-DiHETE (Chiaro et al. (2008), "Leukotriene A4 metabolites are endogenous ligands for the Ah receptor", *Biochemistry* 47, 8445-8455; Machado et al. (2006), "Anti-inflammatory actions of lipoxin A4 and aspirin-trigerred lipoxin are SOCS-2 dependent", *Nature Medicine,* 12, 330-334).

Indeed, in a second study, upon activation of PPARδ using the selective ligand GW501516, without I3C, we observed strong expression of PPARδ in the epidermis within 48 h (FIG. 3c). At later time points, PPARδ was strongly expressed in cells of the spinous layer PPARδ expression was epidermis-specific and did not occur in dermal fibroblasts, endothelia, or skin-associated T cells (see below). PPARδ expression was also inducible by topical application of the AhR ligand indole-3-carbinole to the skin (I3C, FIG. 3d), thereby confirming that epidermal induction is triggered by the AhR-responsive element in the Cyp1A1 promoter. The net effect is a tightly controlled inducible expression of PPARδ in suprabasal mouse epidermis which is comparable to that observed in human psoriasis lesions.

Figure 4:
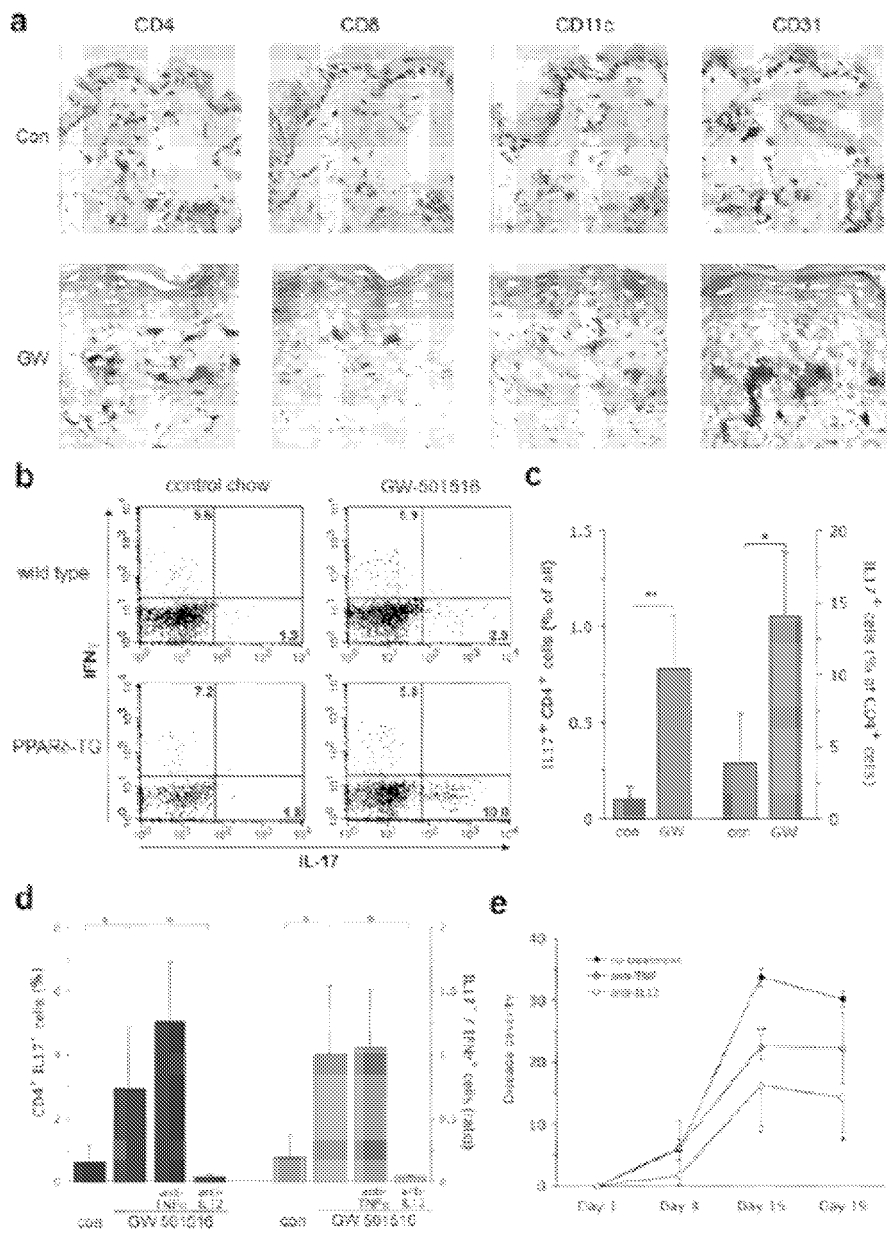
FIG. 4 illustrates immune activation in PPAR(-mediated skin disease. (a) immunohistochemistry for CD4, CD8, CD11c, and CD31 (Pecam 31) of skin from PPAR(-transgenic mice maintained in the absence (top) or presence of GW501516. Magnification 200×, (b) flow cytometry analysis showing intracellular FACS-staining for IFN (and IL17 of skin cells (gated for CD4) from wild type and PPAR (transgenic mice maintained in the presence or absence of GW501516, respectively. Numbers in quadrants indicate frequency of positive cells, (c) frequency of CD4+IL17+ of IL17+ cells (expressed as percent of all CD4+ gated cells) in PPAR (transgenic and C57B1/6 wild type mice maintained in the presence or absence of GW501516 (n=4 per group), as determined by flow cytometry. *p<0.01; **p<0.001, (d) frequency of CD4+IL17+ Th17 cells (left y-axis, black columns) and ratio of IL17+ and IFN(+ cell frequencies (right y-axis, grey columns) in the skin of PPAR (mice maintained in the absence or presence of GW501516 with or without i.p. injection of anti-TNF(, or (IL12/23p40 (n=4, see Methods), (e) disease severity, expressed as mean±s.d., assessed by the degree of erythema, thickening, scaling, and hair loss (see Methods, representative photographs of mice on day 19 post induction are shown in FIG. S6) in PPAR (transgenic mice GW501516—containing chow with or without additional intraperitoneal injection of anti-TNF (or (IL12/23p40 (anti-IL12). *p<0.01, **p<0.001 (treatment vs. control)
Figure 5:
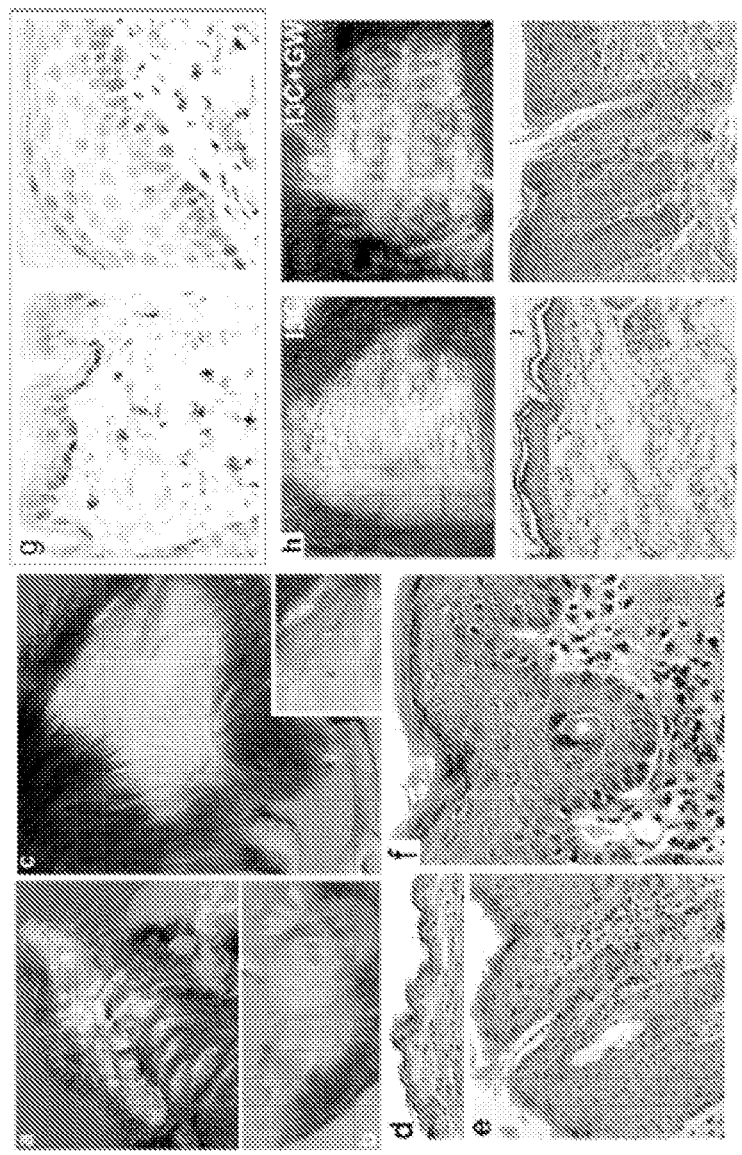
FIG. 5. Skin phenotype in PPARδ transgenic mice twenty days after beginning of GW501516 (GW) administration.

As early as seven days after initiation of PPARδ-activation by GW501516 (GW), scaling, erythema formation, and skin thickening was notable in all PPARδ transgenic mice (FIG. 4a-c). Hyperkeratosis and concomitant hair loss was maximal in regions subjected to mechanical friction, such as abdomen (FIG. 4b, S3), the paws (FIG. 4a), or the chin (FIG. S2). While hyperkeratotic plaques were also noted on the back in some mice (FIG. 4c) changes on the dorsal skin were mostly limited to scaling (FIG. S2). Thus, the extent of clinical changes displayed a pronounced mechanical trigger effect similar to the isomorphic trigger effect seen in psoriasis. Histology showed epidermal thickening (FIG. 4e), dilation of dermal vessels, and a lymphocytic dermal infiltrate. Of note, in contrast to psoriasis, the granular layer was prominent (FIG. 4f), consistent with the known effect of PPARδ on epidermal differentiation. Moreover, K67 staining demonstrated massive hyperproliferation in the basal layer of the epidermis (FIG. 4g). Importantly, these changes were mediated solely by ligand-mediated activation of PPARδ, but not by AhR activation since prolonged administration of a chow containing a very high I3C concentration (0.5% w/w) caused no skin changes in the absence of PPARδ activation (not shown). Likewise, topical administration of I3C to the skin was unable to elicit a phenotype but was effectively replicated by additional topical addition of GW501516 (FIG. 4h). Thus, the skin phenotype in PPARδ transgenic mice is mediated by activation of PPARδ in suprabasal keratinocytes.

In contrast to known animal models, the model of the present invention mimics the clinical and histopathologic characteristics of inflammatory skin conditions, such as human psoriasis, within seven days, offers a highly controllable and rapid disease onset by dose-controlled administration of specific transgene activators, and occurs in virtually all experimental animals. Moreover, the disease occurs as a result of forced upregulation of a protein as it occurs in human psoriasis patients, irrespective of their individual genetic risk profile, thus replicating a pathological signalling event operative in the human disease. Therefore, the model does not merely represent a phenocopy of psoriasis, but re-creates elements of human psoriatic signalling in vivo. Experiments indicate that the model shows the same dynamic plasticity to environmental factors as human psoriasis, for example, a classical Koebner phenomenon is observed leading to highly aggravated disease activity at areas of mechanical friction. Accordingly, the model disclosed herein is useful for studying the immunopathogenesis of human psoriasis, and for evaluating therapeutic agents for ameliorating or preventing inflammatory skin conditions, such as psoriasis. In particular, the model is useful for studying the properties of the epidermis and dermis as a metabolic organ, which have not been well studied to date.

The model is useful for studying the direct or indirect effects of test substances, or screening test substances (such as small chemical entities or biologics) to identify substances which may be useful for the treatment or prevention of psoriasis or other inflammatory skin conditions. A test substance can be administered to the mouse by an appropriate method, such as feeding, gavage, intravenous injection, retro-orbital injection, intra-arterial injection, intra-peritoneal injection or subcutaneous injection. The test substance may be administered to the mouse after transcriptional and conformational activation of PPARδ to investigate the effects of the test substance on psoriatic symptoms which have already developed, after transcription activation but before conformational activation, or before either transcriptional or conformational activation to investigate whether and how the test substance affects or prevents the development of psoriatic symptoms.

In order to determine the efficacy of a test substance as a candidate for the prevention or treatment of psoriasis, or another inflammatory skin condition, the presence of some or all of the following symptoms can be measured on a quantitative or qualitative basis and compared with a suitable control: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, and changes in cytokine and/or gene expression patterns which correspond to changes in cytokine and/or gene expression patterns which are observed in the skin of human patients with psoriasis.

A test substance may be considered to be efficacious if it prevents or reduces the extent of one or more of the above symptoms or, in experiments where the test substance is administered before psoriatic symptoms have developed, a test substance may be considered to be efficacious if it delays the onset of one or more of the above symptoms.

The efficacy of a test substance may be established by visual inspection of symptoms or by measuring the amount, activation or properties of cells which are potentially implicated in the response to PPARδ activation, for example, the amount and activation of regulatory T-cells, dendritic cells, natural killer cells, B-cells, and macrophages. In order to assess the efficacy of a test substance, it may be relevant to measure the amount of antigens such as CD4, CD25, Foxp3, IL17, CD69, B220, DX5, F4/08 and to quantify the production of cells such as CD8 and CD4 cells, or to measure keratinocyte hyperproliferation.

Furthermore, we have found that PPARδ regulates phosphorylayion of signal transducer and activator of transcription 3 (STAT3). STAT3 is hyperphosphorylated in psoriasis and is sufficient to induce a psoriasis-like phenotype in vivo. We found that Tyr-705 phosphorylation of STAT3 was markedly increased in lesional skin of PPARδ transgenic mice (FIG. 6a) and localized to the nuclei of suprabasal cells in the epidermis (FIG. 6b). Inhibition of STAT3 effectively prevented the onset of disease, demonstrating the central role of this pathway (FIG. 6c,d). Strikingly, the single group of genes upregulated in psoriasis while downregulated in PPARδ mice, the interferon response genes have previously been shown to be repressed by STAT3 (FIG. 6e, dark shaded columns), as part of what has been termed the "anti-inflammatory response" (Murray, P. J. (2006), "STAT3-mediated anti-inflammatory signaling." *Biochemical society transactions*, 34, 1028-1031. Indeed, inhibition of STAT3 signalling partially reversed the down-regulation of one of the most repressed transcripts, IFI27 (FIG. 6f), indicating that the inhibition of IFN signalling in PPARδ transgenic mice is mediated in part by STAT3.

Accordingly, the efficacy of a test substance may be assessed by assaying STAT3 phosphorylation, or another biological indicator known to be affected by STAT3 phosphorylation status. This may enable a more rapid initial screen to be carried out than would be the case if it was necessary to wait for a wide range of psoriatic symptoms to be expressed. STAT3 phosphorylation may be assayed using, for example, an antibody which has an affinity for STAT3 which depends on Tyr-705 phosphorylation status.

Examples of suitable test substances include PPARδ antagonists, such as cyclosporin A or CTLA4-IG, as well as libraries of small molecules, peptides, peptidomimetics, antibodies and antibody fragments.

One test substance which may be employed for the prevention or treatment of psoriasis, or another inflammatory skin condition, is methyl 3-({[2-(methoxy)-4-phenyl]amino}sulfonyl)-2-thiophenecarboxylate, known as GSK 0660, or a pharmaceutically acceptable derivative or salt thereof. GSK 0660 is described in Shearer B. G. et al., (2008), "Identification and Characterization of a Selective Peroxisome Proliferator-Activated Receptor β/δ (NR1C2) Antagonist", *Molecular Endocrinology*, 22(2): 523-529, the contents of which are incorporated herein by virtue of this reference. GSK 0660 is available from Sigma-Aldrich (St. Louis, USA), CAS No. 1014691-01-2. GSK 0660 is a highly selective inhibitor of PPARδ. Although GSK 0660 lacks in vivo bioavailability, it may be applied topically for the treatment of psoriasis, or other inflammatory skin conditions. Indeed, the poor in vivo bioavailability may be advantageous as effects will be confined to the skin, reducing or avoiding side effects in other organs.

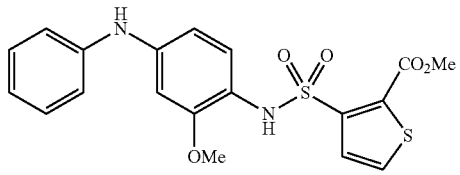

Tissue or cells from the mouse model may also be useful in research. Tissue or cells may be removed from the mouse model after the induction of psoriatic symptoms. Tissue or cells may be removed before transcriptional activation and then PPARδ within the tissue or cells can be transcriptionally and then conformationally activated. Tissue or cells may be removed after transcriptional activation but before conformational activation and then PPARδ within the tissue or cells can be conformationally activated. The difference between the physiological response of isolated tissue or cells types to transcription and/or conformational activation, and their response in vivo can be compared to investigate components of the immune system which are relevant to induction of the skin pathology. Tissue or cells from the mouse model may be investigated in vitro, or transplanted to a host organism, such as a scid mouse.

The model can also be employed to study the effect of PPARδ activation in specific cell subsets. Specific cell types such as subsets of dendritic cells or T lymphocyte subsets, for example generated by in vitro generation, can be transferred to non-transgenic congenic recipient mice in order to evaluate the contribution of PPARδ activation exclusively in the transferred cell subset on the development of an inflammatory skin condition, such as psoriasis, in vivo. The same can also, for example, be performed by grafting skin from PPARδ transgenic animals onto non-transgenic recipient skin.

Instead of employing the CYP1A1 promoter, the overexpression of PPARδ, or the expression of transgenic PPARδ, may be effected using alternative promoters which control expression in relevant tissues. Constitutive and inducible promoters can each be considered. A keratinocyte specific promoter (for example, Keratin 5 or Keratin 14 promoter) may be employed to cause PPARδ to be expressed specifically in keratinocytes. A Th-17 specific promoter (for example, the IL23-R promoter) might also be employed. These may lead to an improved model. Alternatively, it may be essential for PPARδ to be expressed at a sufficiently high level in a range of tissues including, for example, the spleen, in order for symptoms to be displayed. Cell types which may be important or essential for the displayed phenotype include regulator T-cells, so-called Th17 cells, dendritic cells, and natural killer (NK) cells. The promoter should preferably be selected to avoid strong constitutive expression in tissues where the transgene may have substantial toxic effects, e.g. the liver.

Indeed, experiments with an animal model according to the example embodiment have demonstrated strong similarities in gene dysfunction between these mice and human psoriasis. Th17 cells, which cause autoimmune activity in human psoriasis have been found to be upregulated in the mice and a subsequent downregulation of these cells has been found to be correlated with a reduction in symptoms, indicating their importance.

Thus, in summary, the invention provides an animal model useful for research into inflammatory skin conditions, including psoriasis, based upon the recognition that over activation of PPARδ in the skin of animals such as rodents induces an inflammatory skin condition that closely resembles human psoriasis. Although other animal models have been reported for human psoriasis and other inflammatory skin conditions, the animal model of the invention represents the first in vivo experimental system which has induced the expression of a gene known to be expressed in human psoriatic skin but is not expressed in mouse skin (humanized mouse model), can be induced in virtually all experimental animals within four weeks, and does not require the use of human skin or cross implantation of lymphocytes for model generation. Thus, the animal model disclosed herein is not a disease-affected skin transplantation animal model or a T cell transplantation model of an inflammatory skin disease and has significant advantages over these known models.

Further variations and modifications may be made within the scope of the invention herein disclosed.

The invention claimed is:

1. A method of preparing a mouse model for an inflammatory skin condition, the method comprising providing a mouse which expresses transgenic Peroxisome Proliferator-Activated Receptor delta (PPARδ) and administering to the mouse a dose of PPARδ agonist which is sufficient to mediate symptoms characteristic of the inflammatory skin condition.

2. A method as claimed in claim 1, wherein the mouse expresses transgenic human PPARδ.

3. A method as claimed in claim 1, wherein the expression of transgenic PPARδ is inducible and the method comprises the step of inducing the expression of transgenic PPARδ.

4. A method as claimed in claim 1, for preparing a mouse model for psoriasis, wherein the mouse develops symptoms characteristic of psoriasis responsive to administration of the dose of PPARδ agonist.

5. A method as claimed in claim 1, wherein the mouse develops at least eight of the following symptoms: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, changes in cytokine and/or gene expression patterns which correspond to changes in cytokine and/or gene expression patterns which are observed in the skin of human patients with psoriasis.

6. A method as claimed in claim 1, wherein the mouse displays a Koebner phenomenon.

7. A method as claimed in claim 1, wherein the mouse expresses transgenic PPARδ in one or more types of cell, including at least keratinocytes, to thereby display symptoms characteristic of psoriasis.

8. A method as claimed in claim 7, wherein the mouse expresses transgenic PPARδ in at least some types of T cell, to thereby display symptoms characteristic of psoriasis.

9. A method of identifying a substance for use in the treatment of an inflammatory skin condition, the method comprising providing a mouse which expresses transgenic PPARδ, administering a dose of PPARδ agonist which would be sufficient to mediate symptoms characteristic of the inflammatory skin condition in the absence of test substance to the mouse, and administering a test substance to the mouse, or tissues and/or cells derived therefrom.

10. A method as claimed in claim 9, wherein the mouse expresses transgenic human PPARδ.

11. A method as claimed in claim 9, wherein the mouse is of a species, the wild type of which does not express significant amounts of PPARδ in the skin.

12. A method as claimed in claim 9, for identifying a substance for use in the treatment of psoriasis wherein, in the absence of test substance, the mouse would develop symptoms characteristic of psoriasis.

13. A method as claimed in claim 9, wherein, in the absence of test substance, the mouse would develop at least eight of the following symptoms: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, and changes in cytokine and/or gene expression patterns which correspond to changes in cytokine and/or gene expression patterns which are observed in the skin of human patients with psoriasis.

14. A method as claimed in claim 9, wherein, in the absence of test substance, the mouse displays a Koebner phenomenon.

15. A method as claimed in claim 9, comprising the step of assaying the phosphorylation of STAT3, or measuring another biological indicator linked to the activation state of STAT3.

16. A method as claimed in claim 9, wherein symptoms characteristic of the inflammatory skin condition in the mouse, or the tissue and/or cells derived from a said mouse, are compared with a control to which the test substance is not administered, or is administered in a different amount.

17. A method as claimed in claim 9, wherein the mouse expresses transgenic PPARδ in one or more types of cell, including at least keratinocytes or within the sebaceous glands.

18. A method as claimed in claim 17, wherein the mouse expresses transgenic PPARδ in at least some types of T-cell.

19. A transgenic mouse, in which at least some types of cell, including at least keratinocytes, express transgenic PPARδ in sufficient amount for the mouse to display symptoms characteristic of an inflammatory skin condition in the presence of a PPARδ agonist.

20. A transgenic mouse as claimed in claim 19, wherein the expression of transgenic PPARδ is inducible, and wherein the mouse does not display symptoms characteristic of psoriasis except when the expression of transgenic PPARδ is induced and a PPARδ agonist is present.

21. A transgenic mouse as claimed in claim 20, which displays symptoms characteristic of psoriasis in the presence of a PPARδ agonist.

22. A transgenic mouse as claimed in claim 21, which displays at least eight of the following symptoms, in the presence of a PPARδ agonist: erythematous skin with loose whitish scales; acanthosis, hyperkeratosis and focal parakeratosis; keratinocyte hyperproliferation; changes in keratinocyte differentiation; dermal angiogenesis; infiltration of CD4+ and CD8+ T lymphocytes; dilation of blood vessels; increased number of dermal mast cells; infiltration of the dermis with neutrophils; formation of microabscesses within the epidermis; increased numbers of CD11c+ dendritic cells in the dermis, and changes in cytokine and/or gene expression patterns which correspond to changes in cytokine and/or gene expression patterns which are observed in the skin of human patients with psoriasis.

* * * * *